United States Patent
Skofenko

(10) Patent No.: US 11,832,742 B1
(45) Date of Patent: Dec. 5, 2023

(54) SLEEPING SENSORY BLANKET WITH CALMING LIGHTS AND METHODS FOR OPERATING THEREOF

(71) Applicant: Ivan Skofenko, Whitehorse (CA)

(72) Inventor: Ivan Skofenko, Whitehorse (CA)

(*) Notice: Subject to any disclaimer, the term of this patent is extended or adjusted under 35 U.S.C. 154(b) by 0 days.

(21) Appl. No.: 18/195,869

(22) Filed: May 10, 2023

(51) Int. Cl.
| | |
|---|---|
| A47G 9/02 | (2006.01) |
| F21V 23/00 | (2015.01) |
| F21V 23/04 | (2006.01) |
| F21V 23/06 | (2006.01) |
| F21W 131/30 | (2006.01) |
| F21Y 115/10 | (2016.01) |
| F21V 23/02 | (2006.01) |

(52) U.S. Cl.
CPC .......... *A47G 9/0223* (2013.01); *F21V 23/003* (2013.01); *F21V 23/023* (2013.01); *F21V 23/04* (2013.01); *F21V 23/06* (2013.01); *A47G 2200/08* (2013.01); *F21W 2131/30* (2013.01); *F21Y 2115/10* (2016.08)

(58) Field of Classification Search
CPC .............. A47G 9/0223; A47G 2200/08; F21V 23/003; F21V 23/023; F21V 23/04; F21V 23/06; F21W 2131/30; F21Y 2115/10
See application file for complete search history.

(56) References Cited

U.S. PATENT DOCUMENTS

| | | |
|---|---|---|
| 4,164,008 A | 8/1979 | Miller et al. |
| 4,570,206 A | 2/1986 | Deutsch |
| 4,759,090 A | 7/1988 | Sachetti |
| 4,774,434 A | 9/1988 | Bennion |
| 4,972,533 A | 11/1990 | Brown |
| 5,072,429 A | 12/1991 | Mair |
| 5,375,044 A | 12/1994 | Guritz |
| 6,311,350 B1 | 11/2001 | Kaiserman et al. |
| 6,402,336 B1 * | 6/2002 | Reese ................. F21S 4/10 362/812 |
| 6,511,198 B1 | 1/2003 | Erickson |
| 8,973,182 B2 | 3/2015 | Crucs |
| 10,149,550 B1 | 12/2018 | Bain |
| 2003/0234247 A1* | 12/2003 | Stern ................. H05B 1/0272 219/494 |

(Continued)

FOREIGN PATENT DOCUMENTS

| | | | |
|---|---|---|---|
| CN | 202739465 U | * 2/2013 | |
| CN | 102203336 B | * 5/2015 | ......... A47G 27/0243 |

(Continued)

*Primary Examiner* — Zheng Song
*Assistant Examiner* — Glenn Zimmerman
(74) *Attorney, Agent, or Firm* — Boris Leschinsky

(57) ABSTRACT

A sleeping sensory blanket includes a blanket layer and a plurality of waterproof LED lights attached thereto. The lights are arranged along a strip cable configured for powering the lights. The external pocket of the blanket is sized to accept one end of the strip cable, and a battery-operated controller detachably attached to the strip cable to facilitate its removal and washing of the blanket. The connector between the controller and the strip cable is water-resistant. The controller is configured for timed activation of the plurality of LED lights in a sleeping mode with an LED light brightness at or below a predefined LED light brightness threshold and with at least one predetermined transition from a first light pattern to a second light pattern.

19 Claims, 3 Drawing Sheets

(56) References Cited

U.S. PATENT DOCUMENTS

| | | | |
|---|---|---|---|
| 2006/0001727 A1* | 1/2006 | Haas | A41D 13/0051 |
| | | | 347/194 |
| 2006/0285327 A1 | 12/2006 | Abraham et al. | |
| 2010/0035509 A1* | 2/2010 | Lei | A63H 3/14 |
| | | | 446/327 |
| 2011/0247136 A1* | 10/2011 | Crucs | A47G 9/0215 |
| | | | 5/482 |
| 2012/0327634 A1* | 12/2012 | Aranda | F21V 33/0004 |
| | | | 362/103 |
| 2019/0037658 A1* | 1/2019 | LaDouceur | F21V 33/0004 |
| 2021/0100378 A1* | 4/2021 | Youngblood | A61F 7/007 |

FOREIGN PATENT DOCUMENTS

| | | | |
|---|---|---|---|
| CN | 206006812 U | * | 3/2017 |
| FR | 3106052 A1 | * | 7/2021 |

\* cited by examiner

SLEEPING SENSORY BLANKET WITH CALMING LIGHTS AND METHODS FOR OPERATING THEREOF

BACKGROUND

Without limiting the scope of the invention, its background is described in connection with sleeping blankets. More particularly, the invention describes a sleeping sensory blanket equipped with calming lights to help the user to fall asleep.

Many people have a difficult time falling and staying asleep. The problem is especially acute in some children, in particular those that are afraid of the dark. Sleeping problems with kids can often be attributed to sleeping anxiety and fears, such as fear of the dark. The fear of the dark is a common issue that many children face, and it can make bedtime a particularly stressful experience. Children may have trouble falling asleep, wake up frequently during the night, or even refuse to sleep in their own bed. In some cases, children may even experience nightmares or night terrors, making it even more challenging to get a good night's rest. To help alleviate these fears, parents can take several steps, such as using a night light or providing a stuffed animal, that provides sensory stimulation and comforting effect.

A night light can emit a soft, warm glow, which can be comforting and soothing for children and adults. The light can be placed in a strategic spot in the room, such as near the child's bed or in a corner, to provide enough illumination without being too bright to disturb sleep. The warm light sensory stimulation can help the child feel safe and secure in their own space. A changing light can adds positive experience to the nighttime routine, which can help distract the child from their fear. A changing light can cycle through different colors, patterns, or scenes, which can be exciting for the child to watch. This type of light can also be used as a night light and provide a calming and soothing atmosphere for the child. Using night lights and changing lights can be an effective strategy to help a child overcome their fear of the dark. It can provide a sense of comfort, security, and entertainment for the child, which can help them relax and fall asleep more easily.

These simple remedies have their limitations. A night light is typically a single light fixture that is located away from the bed. It may be more effective to bring the light glow as close to the child as possible. In addition, it may be advantageous to use the lights such that they cover as much of a vicinity surrounding the child as practical. The lights incorporated into the blanket create a combination of visual- and touch-sensory stimuli that can provide a positive, comforting experience to adults and children.

Decorative bedding and blankets with imprinted scenes are also known. For example, for children, cartoon characters or action figures may be represented. It is also known to incorporate light and sound elements into bedding, the light elements positioned atop the bedding to represent features such as the eyes of a creature. It is further known to affix a light-emitting phosphorescent material to bedding to display a pattern in the dark for a period of time following illumination. In addition, the phosphorescent material needs to be charged with a strong light, such as direct light or a special torch, before it starts emitting light.

The need exists to provide blankets and general bedding that is decorative, amusing, and comforting, and includes entertainment elements. The need further includes providing a sleeping blanket that can be activated without charging with light to provide different lighting scenes and patterns to provide sensory stimulation and activate the positive imagination of the user. It would also be desirable to provide such blankets that are machine washable and can withstand moisture without damaging the lights.

SUMMARY

Accordingly, it is an object of the present invention to overcome these and other drawbacks of the prior art by providing a novel sleeping blanket configured for providing calming lights near the user and distributed throughout the bed to provide enhanced comforting effect due to a combination of visual and touch sensory stimuli.

It is another object of the present invention to provide a novel sleeping blanket that can be washed, either manually or using a washing machine, without compromising the integrity of the electronic parts.

It is a further object of the present invention to provide a novel sleeping blanket that can change the lighting patterns throughout the operational time.

It is yet a further object of the present invention to provide a sleeping blanket that can operate automatically without having to turn the controller on or off.

The sleeping blanket of the invention includes a blanket layer featuring a plurality of waterproof LED lights attached thereto. The LED lights are arranged along a strip cable configured for powering the lights. The blanket may include an external pocket, which may be opened and closed, for example, by one or more buttons, a zipper, or another fastener. The external pocket may be sized to accept one end of the strip cable and a battery-operated controller, which may be detachably attached to the strip cable and configured to operate the plurality of LED lights. The connector between the controller and the strip cable may be made to be water-resistant.

The controller is configured for separating from the strip cable when a first part of the detachable connector is separated from a second part thereof, thereby facilitating removal of the controller and washing of the sleeping blanket without compromising the integrity of the plurality of LED lights. The controller is also configured for timed activation of the plurality of LED lights in a sleeping mode with an LED light brightness at or below a predefined LED light brightness threshold and with at least one predetermined transition from a first light pattern to a second light pattern.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

Figure 1:
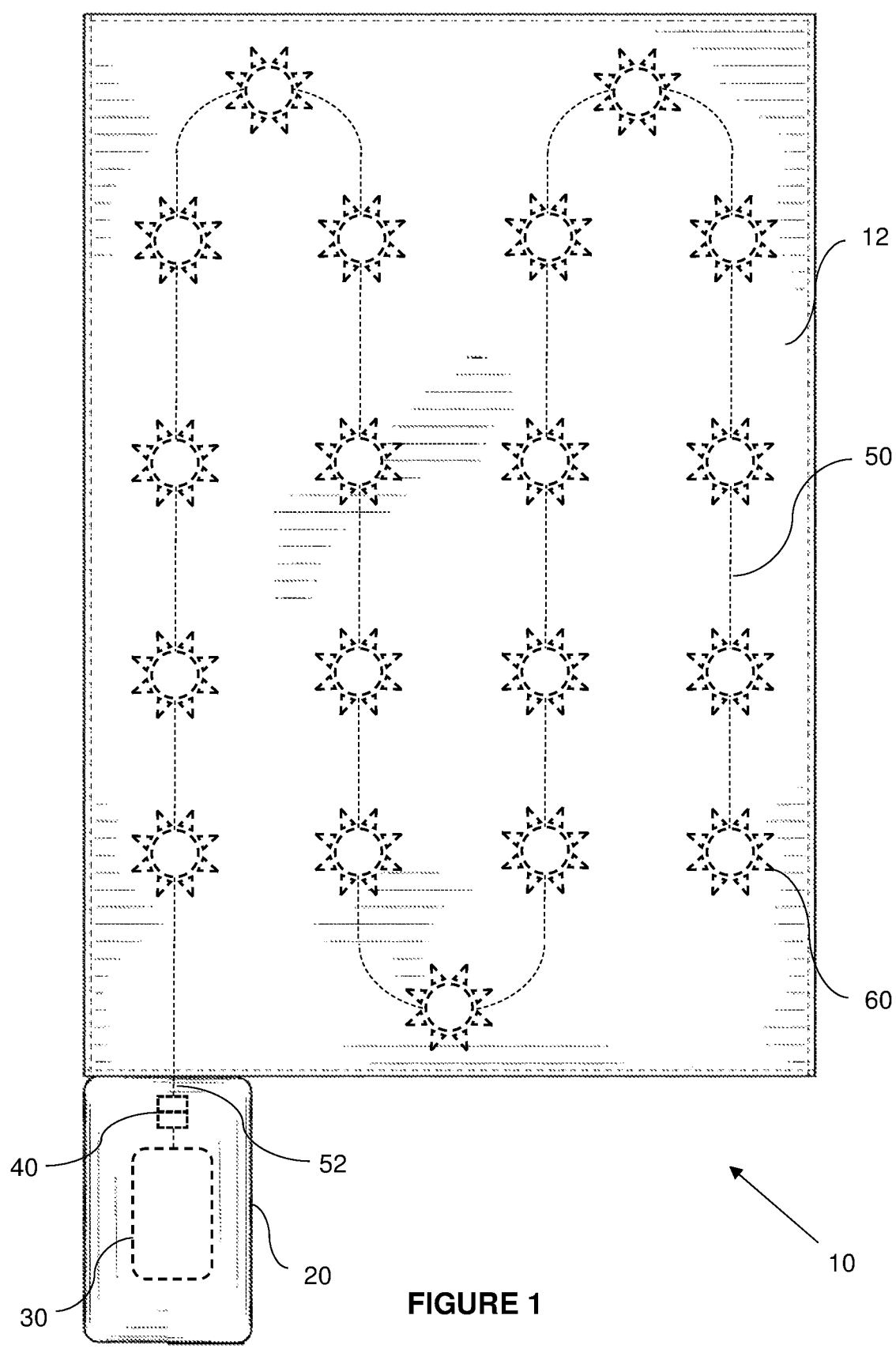
FIG. 1 is a top view of the sleeping blanket showing a serpentine arrangement
of LED lights.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 2:
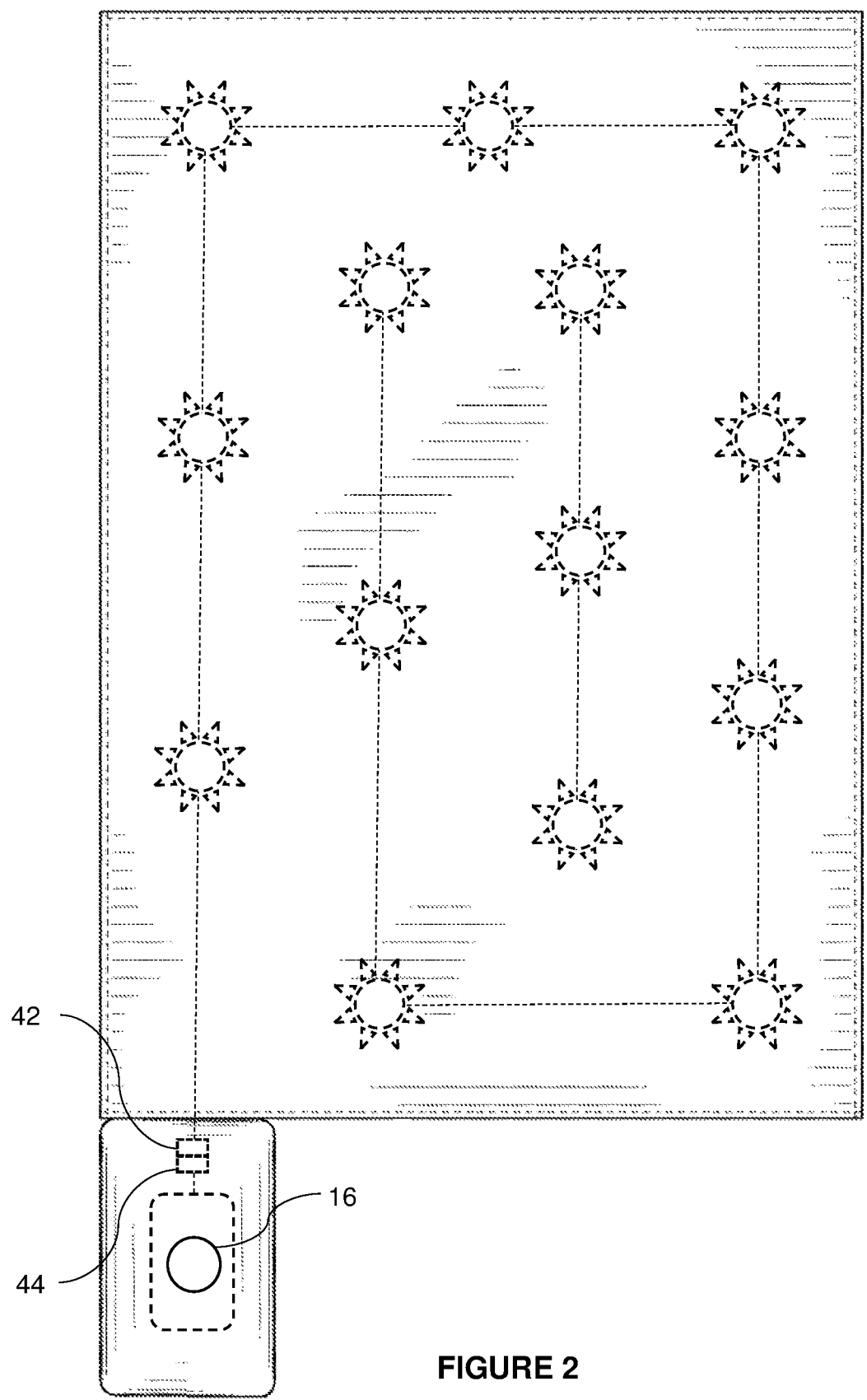
FIG. 2 is a top view of the sleeping blanket showing a spiral arrangement of LED lights.

FIGS. 1 and 2 show a sleeping blanket 10 with a plurality of LED lights 60 attached thereto and located along at least one strip cable 50. The term "sleeping blanket" is used herein to broadly describe blankets, bed throws, duvets, comforters, covers thereof, and other bedding items, as the invention is not limited in this regard to just a blanket itself. The blanket 10 may include a single blanket layer 12 or may comprise several layers, including blanket covers, blanket sheets, etc., on one side or on both sides of the blanket.

One, several, or all individual lights 60 may be attached to the external layer or a single layer 12 of the sleeping blanket 10 to face away therefrom and project the light on one side of the blanket 10. In other embodiments, one, some, or all LED lights 60 may be attached to the blanket layer 12 to project the light on both sides of the blanket. In embodiments, a total of 4 to 100 LED lights may be used, such as at least 4, at least 5, at least 6, at least 8, at least 10, at least 12, at least 15, at least 20, at least 25, at least 30, at least 40, at least 50, at least 60, at least 70, at least 80, at least 90, 100, or even more LED lights, as the invention is not limited in this regard. More than one strip cable 50 may also be used to operate and illuminate the plurality of LED lights 60.

The plurality of LED lights 60 may be configured to change the color and intensity of the light emanated therefrom, as selected by controller 30 described below. One, several, or all of the LED lights may be controlled and operated individually or in groups so as to provide adjustable light patterns.

The strip cable 50 may include two or more electrical conductors encapsulated within one or more polymer layers for insulation purposes. Led lights may also be embedded in the same polymer layer as the strip cable 50, thereby providing a waterproof configuration for the strip cable 50 and the plurality of LED lights 60. The strip cable 50 and the plurality of LED lights 60 arranged along thereof may be attached to the blanket layer 12 by stitching, sewing, stapling, riveting, buttons, or by other fasteners. The strip cable 50 may be positioned along a predetermined pattern, such as a serpentine pattern shown in FIG. 1 or a spiral pattern shown in FIG. 2. Other configurations of Led lights positions may be used to locate the lights either throughout the blanket 10 or at a desired portion thereof, as the invention is not limited in this regard.

An external pocket 20 may be provided as part of the sleeping blanket 10. In embodiments, the external pocket 20 may be provided with a fastener configured to allow for the closing and opening of the external pocket 20. Examples of suitable fasteners may include one or more buttons or snaps, a fastener, an elastic cord, or a simple foldable flap. The external pocket 20 may be inverted to form an internal pocket of the blanket 10 so as to preserve a generally rectangular overall shape thereof. In other embodiments, the external pocket may remain outside the blanket 10, as seen in FIGS. 1 and 2. The external pocket may be sized to be sufficient to accept the controller 30 and the detachable connector 40 within thereof. In one example, the external pocket may be sized to be at least 2 inches long and at least 1 inch wide. In other embodiments, the length and the width of the external pocket may be between 1 and 8 inches, as the invention is not limited in this regard. In further embodiments, the external pocket may not have a rectangular shape but may have an oval shape, a round, shape, or another suitable shape to retain the controller 30 and the connector 40 inside thereof.

The external pocket 20 may be attached along the edge of the sleeping blanket 10, for example, at one corner thereof, although other locations are also contemplated in this invention. One example of such another location is in a central portion of the blanket and on top of the main blanket layer 12 (not shown in the drawings). This alternative location may be advantageous in case the controller 30 is made to be small and light so as to not present a clearly palpable piece of hardware for the user of the sleeping blanket 10.

One end of the strip cable 50 is made to enter the internal space of the external pocket 20. A first part 42 of the detachable connector 40 is attached to the end of the strip cable 50. At least the first part or both the first part 42 and the second part 44 of the connector 40 are made to be water-resistant, so as to preserve the integrity of the strip cable 50 and the plurality of LED lights 60 when the blanket 10 is washed, including washing in a washing machine at the most aggressive cycle selection. Both the first and the second parts, 42 and 44, of connector 40 may be connected together to complete the electrical circuit to power the LED lights using controller 30. This connection may be made with an optional latch or with sufficient friction to ensure that the connection is not broken accidentally.

Figure 3:
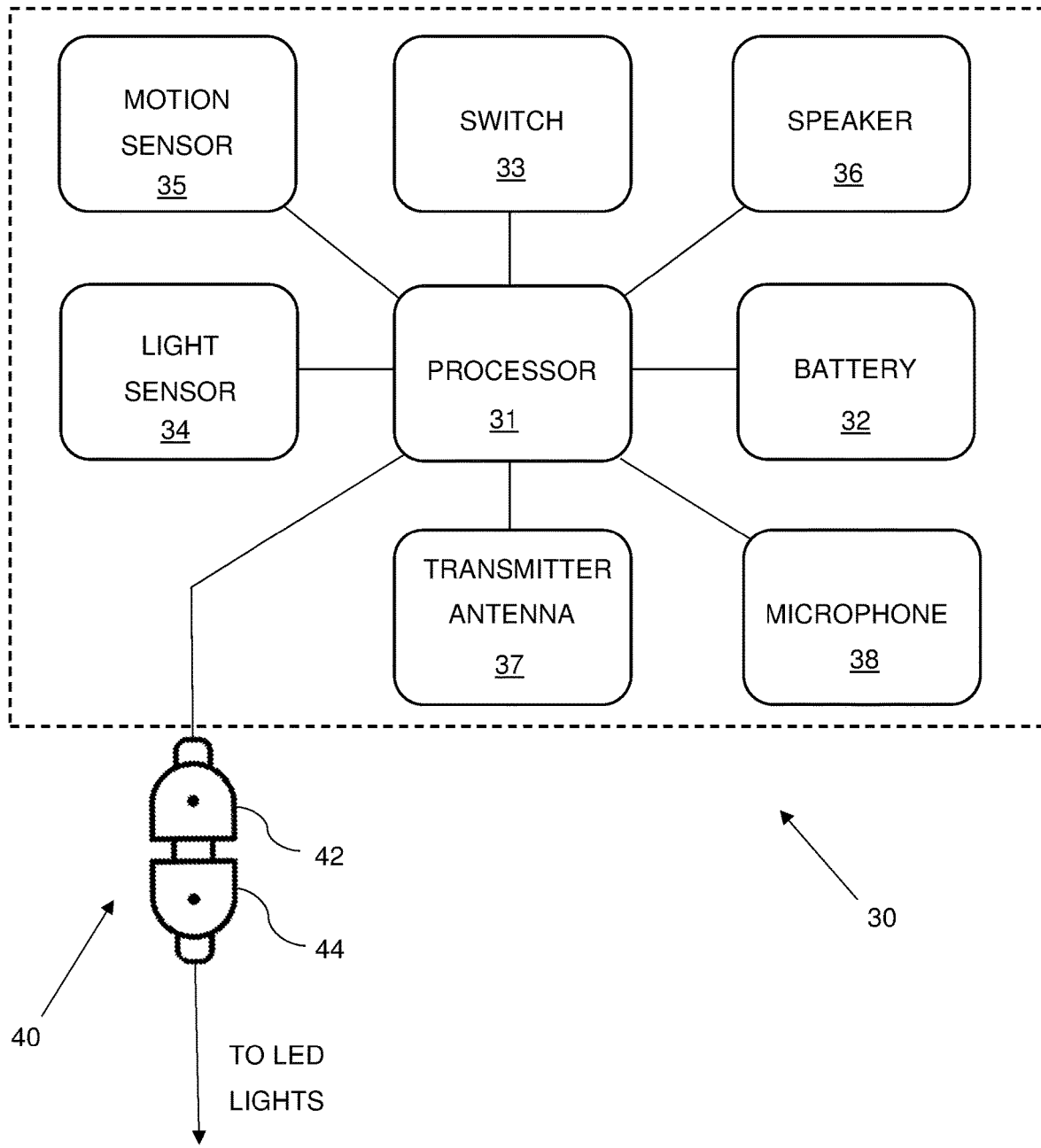
FIG. 3 shows a block-diagram of the controller for operating the plurality of LED lights.

The controller 30 is now described in greater detail with reference to FIG. 3. It may include a suitable processor 31, which may be energized by one or more batteries 32. The battery 32 may be a single-use or rechargeable battery. The controller 30 may also be powered using a plug-in cable using a suitable power supply.

A manual switch 33 may also be provided and configured to allow turning the controller 30 on or off. In one embodiment, the switch 33 may be a push button. Upon initial activation by the manual switch 33, the processor 31 may be configured to operate the plurality of LED lights for a predetermined period of time and automatically turn off afterward. For example, once operation of LED lights 60 is initiated, the processor 31 may be configured for timed activation of the plurality of LED lights in a sleeping mode. The timed activation may be configured to operate the LED lights for a predetermined time of 3 to 30 min, such as at least 3 min, at least 5 min, at least 7 min, at least 10 min, at least min, at least 20 min, at least 25 min, at least 30 min, or another desired duration. The timed activation may be a fixed number of minutes, or it may be adjustable by the user, for example, using a smartphone application associated with the controller 30.

LED light brightness may be set by the controller 30 at or below a predefined LED light brightness threshold. The optimum light brightness for a good night's sleep varies depending on individual preferences and circumstances, so the sleeping sensory blanket provides for light adjustments to suit the individual needs of the user. In general, however, it is recommended to have a dim and low-level light in the bedroom. In embodiments, the plurality of LED lights may be operated to provide an overall light level in the bedroom of lux or less, which is roughly equivalent to the level of light given off by a single candle. It is also generally known that blue light, which is emitted by electronic devices such as smartphones and tablets, can be particularly disruptive to sleep. In embodiments, the plurality of LED lights may be operated to produce light in colors other than blue to promote better sleep. LED light operation may proceed with at least one predetermined transition from a first light pattern to a second light pattern.

The first light pattern may be different from the second light pattern in the color of the LEDs, the number of the LEDs that are activated, or any other light pattern characteristic. For example, the first light pattern may be activating every other LED, and the second light pattern may be activating the remaining LEDs and turning off the LEDs of the first light pattern. Another example is activating all LEDs in blue light for the first light pattern and gradually switching the color to green for the second light pattern.

More than two light patterns may be used throughout the timed activation of the LED lights 60. As can be appreciated by a person skilled in the art, there are many calming light patterns that may be suitable for the current invention. The controller 30 may be preprogrammed to operate the LED lights 60 in one or more predetermined calming light sequences of light patterns. Alternatively, the sequence of light patterns may be selected or adjusted by the user, for example, using a smartphone app as described below, as the invention is not limited in this regard.

The controller 30 may be further configured to operate the LED lights in a waking mode with an LED light brightness at or above the predefined LED light brightness threshold. The LED lights may be operated to wake up the user with at least one predetermined transition from a third light pattern to a fourth light pattern. One example of this is flashing all LED lights on and off at maximum brightness, which may cause the user to wake up. In further embodiments, the waking mode may be introduced gradually with a slow increase in brightness and/or a slow ramp-up of transition speed between the light patterns. The waking mode may be disconnected by the user pushing on the manual switch or after a predetermined period of time.

The controller 30 may further optionally include an ambient light sensor 34. Upon detection by the ambient light sensor 34 of ambient light switched off, the controller 30 may be configured to initiate operation the plurality of LED lights automatically and for a predetermined period of time. Once the time of operation expires as described above, the controller 30 may be configured to turn the LED lights off automatically. Using the ambient light sensor may allow the entire operation of the sleeping blanket to be fully automatic, thus obviating the need for a child or a caregiver to turn the LEDs controller 30 on or off manually. Initiation of the operation may be simply triggered by the caregiver turning the lights off in the child's bedroom. The external pocket may include an opening 16 to expose the ambient light sensor 34 to room lights.

The controller 30 of the sleeping blanket 10 may further include a motion sensor 35 incorporated therein. The motion sensor 35 may be configured to detect the movement of the blanket, which may be a result of the movement of the user. Distinction between the user being asleep or awake may be done by detecting movements of the user respectively below or above a predetermined movement threshold. Movement pattern recognition, coupled with the ambient light sensor and/or a timer equipped with information about a desired sleep time, may be used to detect whether the user is awakened in the middle of the night. Detection of such an event may be used to automatically operate the controller 30 to initiate another timed activation of the LED lights to calm the user down and help to fall asleep. If the motion pattern indicates that the user is not asleep, the controller may be configured to continue operating the plurality of LED lights 60 until the motion sensor indicates that the user is asleep.

In other embodiments, the motion sensor 35 may be used to automatically determine the duration of the LED lights activation. Instead of the timed duration where the controller 30 is configured to switch the LED lights after a predetermined period of time, in this configuration, the LED lights are operated continuously or intermittently until the motion pattern is indicative of the user being asleep.

In further embodiments, the controller 30 may further include a built-in microphone 38. The controller 30 may be configured to turn the LED lights on or off using the voice command detected by the microphone 38. This may be more convenient than operating the controller 30 using the manual switch 33. The microphone signal may be further wirelessly transmitted by the controller 30 using an antenna 37 to a baby monitor or a smartphone in another room (not shown) to monitor the child's sleep by a parent or a caregiver.

The controller 30 may further comprise a wireless transmitter with antenna 37. Using a wireless transmitter 37 opens many opportunities to improve the performance of the controller 30. In one embodiment, the wireless transmitter 37 may be used to operate the processor 31 using an external device such as a smartphone equipped with a corresponding software application, in which the smartphone is connected to the controller 30 via a wireless link. Using this software application may allow setting and adjusting various parameters of blanket operation, such as:

a first and a second light patterns,
LED lights brightness,
timing for turning the LED lights on and off, etc.
a duration of operating the plurality of LED lights, etc.

In other embodiments, the smartphone app may be used to collect sleeping movement patterns and analyze the quality of sleep using the motion sensor 35. In further yet embodiments, the smartphone app may be used as a baby monitor to transmit sounds recorded by the microphone 38. In addition to the smartphone, other examples of an external device suitable for controlling the operation of the processor 31 include a tablet, a laptop, a computer, a smartwatch, or any device configured for such wireless interaction.

The external device may be further used to set a schedule of operating the plurality of LED lights in the sleeping mode and in the waking mode. The software application may use the timer of the external device to activate and deactivate either one or both the sleeping mode and the waking mode of the controller 30.

A speaker 36 may also be included in the controller 30. The speaker may be used to play a soothing sound during the operation of the plurality of LED lights, such as in a synchronized manner. In further embodiments, using the speaker and the microphone, the controller 30 may be configured for two-way audio communication between a child and a parent or a caregiver in another room, similar to that of a baby monitor. The use of a baby monitor may be replaced with a wireless connection between the sleeping blanket and one or more external devices, such as smartphones or tablets, for example, one for each parent or caregiver if they are located in different places. The child may then speak and hear from more than one parent or caregiver at the same time.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Incorporation by reference is limited such that no subject matter is incorporated that is contrary to the explicit disclosure herein, no claims included in the documents are incorporated by reference herein, and any definitions provided in the documents are not incorporated by reference herein unless expressly included herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A sleeping sensory blanket comprising:
    a blanket layer with an external closable pocket,
    a plurality of waterproof LED lights attached to the blanket layer and arranged along a strip cable configured for powering the plurality of LED lights, one end of the strip cable extending into the external pocket and equipped with a first water-resistant part of a detachable connector, and
    a battery-powered controller removably placed in the external pocket, the controller further comprising a second part of the detachable connector configured to detachably attach to the first part thereof to complete an electrical circuit for powering the plurality of LED lights,
    wherein the controller is configured for separating from the strip cable when the first part of the detachable connector is separated from the second part thereof, thereby facilitating washing of the sleeping blanket without compromising the integrity of the plurality of LED lights, and
    wherein the controller is configured for timed activation of the plurality of LED lights in a sleeping mode with an LED light brightness at or below a predefined LED light brightness threshold and with at least one predetermined transition from a first light pattern to a second light pattern.

2. The sleeping sensory blanket, as in claim 1, wherein the controller comprises a manual switch, the controller is configured upon initial activation by the manual switch to operate the plurality of LED lights for a predetermined period of time and automatically turn off afterward.

3. The sleeping sensory blanket, as in claim 1, wherein the controller further comprises an ambient light sensor, wherein upon detection of ambient light switched off, the controller is configured to operate the plurality of LED lights for a predetermined period of time and automatically turn off afterward.

4. The sleeping sensory blanket, as in claim 1, wherein the plurality of LED lights is configured to project light on one side of the blanket layer.

5. The sleeping sensory blanket, as in claim 1, wherein the plurality of LED lights is configured to project light on both sides of the blanket layer.

6. The sleeping sensory blanket, as in claim 1, wherein the controller further comprising a motion sensor.

7. The sleeping sensory blanket, as in claim 6, wherein the controller is configured to operate the plurality of LED lights for a predetermined period of time and automatically turn off afterward upon detecting motion above the predetermined motion threshold using the motion sensor.

8. The sleeping sensory blanket, as in claim 1, wherein the controller further comprises a microphone, the controller is configured for operation responsive to voice commands as detected by the microphone.

9. The sleeping sensory blanket, as in claim 1, wherein the controller further comprises a wireless transmitter configured to facilitate operation of thereof from an external device, operably connected to the controller via a wireless link.

10. The sleeping sensory blanket, as in claim 9, wherein the external device is a smartphone, a tablet, or a computer.

11. The sleeping sensory blanket, as in claim 10, wherein the operation of the controller is done via a corresponding software application on the external device.

12. The sleeping sensory blanket as in claim 11, wherein any one of the following control parameters is set using the external device: a time to turn the plurality of LED lights on and off, a duration of operating the plurality of LED lights, the LED light brightness, the first light pattern, and the second light pattern.

13. The sleeping sensory blanket, as in claim 1, wherein the controller is further configured to operate the LED lights in a waking mode with an LED light brightness at or above the predefined LED light brightness threshold and with at least one predetermined transition from a third light pattern to a fourth light pattern.

14. The sleeping sensory blanket, as in claim 13, wherein the external device is used to schedule operating the plurality of LED lights in the sleeping mode and in the waking mode.

15. The sleeping sensory blanket, as in claim 1, wherein the controller further comprising a speaker.

16. The sleeping sensory blanket, as in claim 15, wherein the controller is further configured to play a soothing sound using the speaker and operate the plurality of LED lights in a manner corresponding to or synchronized with the soothing sound.

17. The sleeping sensory blanket, as in claim 15, wherein the controller is further configured to play a sound from an external device through the speaker of the controller while operating the plurality of LED lights.

18. The sleeping sensory blanket, as in claim 15, wherein the controller is further configured to use a microphone, the speaker, and a wireless connection to the external device to provide a two-way audio communication, thereby facilitating using thereof as a baby monitor.

19. The sleeping sensory blanket as in claim 1, wherein while in sleeping mode, the plurality of LED lights is operated to avoid blue light.

\* \* \* \* \*